United States Patent [19]

Bühler et al.

[11] 4,349,564
[45] Sep. 14, 1982

[54] USE OF 1,2-DIMETHYL-3-FLUORO-, 1-METHYL-3,3-DIFLUORO-, AND 1,2-DIMETHYL-3,3-DIFLUORO-CYCLOBUTANE-1,2-DICARBONIC ACID 3,5-DICHLOROPHENYL IMIDES AS PLANT FUNGICIDES

[75] Inventors: Niklaus Bühler, Rheinfelden; Marcus Baumann, Basel; Daniel Bellus, Riehen; Elmar Sturm, Aesch, all of Switzerland

[73] Assignee: Ciba-Geigy Corporation, Ardsley, N.Y.

[21] Appl. No.: 141,746

[22] Filed: Apr. 18, 1980

[30] Foreign Application Priority Data

Apr. 20, 1979 [CH] Switzerland ............... 3748/79
Mar. 31, 1980 [CH] Switzerland ............... 2539/80

[51] Int. Cl.³ .................. C07D 209/52; A01N 43/38
[52] U.S. Cl. ........................... 424/274; 260/326.5 B; 204/158 R
[58] Field of Search ............... 260/326.5 B; 424/274

[56] References Cited

U.S. PATENT DOCUMENTS 3,549,655 12/1970 Bublitz .................. 260/326.5 B

FOREIGN PATENT DOCUMENTS 1395 8/1978 European Pat. Off. .

Primary Examiner—David B. Springer
Attorney, Agent, or Firm—Frederick H. Rabin

[57] ABSTRACT

Cyclobutanecarboxylic acid imides of the formula I

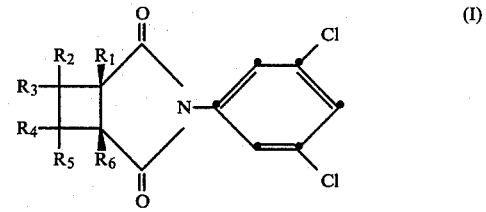

wherein one of $R_1$ and $R_6$ is hydrogen, methyl or ethyl, and the other is methyl or ethyl, $R_2$ and $R_3$ independently of one another are each hydrogen, fluorine or methyl, or $R_2$ is acetoxy or chlorine while $R_3$ is hydrogen, and wherein $R_4$ is hydrogen, methyl or chlorine, and $R_5$ is hydrogen or methyl, whereby $R_3$ and $R_4$ together can also form an additional bond in the four-membered ring, are suitable for combating various fungi and have a particularly excellent action against Botrytis. They can be produced in an especially advantageous manner by photochemical [2+2] cycloaddition of alkenes or alkynes with for example appropriately substituted maleic acid-(3,5-dichlorophenyl)imides.

3 Claims, No Drawings

USE OF 1,2-DIMETHYL-3-FLUORO-, 1-METHYL-3,3-DIFLUORO-, AND 1,2-DIMETHYL-3,3-DIFLUORO-CYCLOBUTANE-1,2-DICARBONIC ACID 3,5-DICHLOROPHENYL IMIDES AS PLANT FUNGICIDES

The present invention relates to novel cyclobutanedicarboxylic acid imides, to processes for producing them, to fungicidal compositions containing such compounds as active substance, as well as to the use of these compounds for combating fungi.

It is known from the JA-Patent Publication (unexamined) No. 74/71 141 that 3,5-dihalogenophenylcyclobutanedicarboxylic acid imides which are unsubstituted on the cyclobutane ring have antimicrobial properties, inter alia also fungicidal properties, and are suitable for example for combating fungus diseases on rice plants. The spectrum of activity of these 3,5-dihalogenophenylcyclobutanedicarboxylic acid imides is however limited. Thus, for example, 3,5-dichlorophenylcyclobutanedicarboxylic acid imide has only a weak action against Botrytis.

It has been shown that the compounds of the formula I according to the invention have excellent fungicidal properties

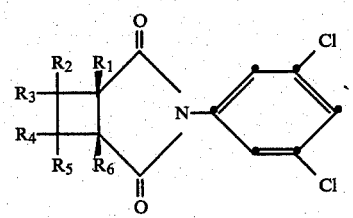

wherein one of $R_1$ and $R_6$ is hydrogen, methyl or ethyl, and the other is methyl or ethyl, $R_2$ and $R_3$ independently of one another are each hydrogen, fluorine or methyl, or $R_2$ is acetoxy or chlorine whilst $R_3$ is hydrogen, and wherein $R_4$ is hydrogen, methyl or chlorine, and $R_5$ is hydrogen or methyl, whereby $R_3$ and $R_4$ together can also form an additional bond in the four-membered ring.

Compounds of the formula I surprisingly have pronounced activity against Botrytis. Botrytis spp. (*Botrytis cinerea, Botrytis allii*) constitutes, with grey mould on grape vines, strawberries, apples, onions and other fruit and vegetable varieties, a considerable economic loss factor.

The compounds of the formula I have a very favourable spectrum of action for practical requirements for the protection of cultivated plants, without affecting the plants disadvantageously by causing undesirable secondary effects. Cultivated plants within the scope of the present invention are for example: cereals, maize, rice, vegetables, sugar beet, soya bean, groundnuts, fruit trees, ornamental plants, grape vines, hops, Cucurbitaceae (cucumbers, pumpkins and melons), Solanaceae, such as potatoes, tomatoes and tobacco, as well as banana, cocoa and natural rubber plants.

Fungi occurring on plants or on parts of plants (fruit, blossom, foliage, stalks, tubers or roots) of the said crops and of related cultivated crops can be inhibited or destroyed with the active substances of the formula I, and also parts of plants subsequently growing remain preserved from such fungi. The active substances are effective against phytopathogenic fungi belonging to the following classes: Ascomycetes (for example Erysiphaceae, Fusarium or Helminthosporium); Basidiomycetes, such as in particular rust fungi (for example Puccinia and Tilletia); Fungi imperfecti (for example Moniliales and others, Cercospora, Sclerotinia and also Botrytis and Piricularia); and against Oomycetes belonging to the Phycomycetes class, such as Phytophthora or Plasmopara. The said active substances can also be used as dressing agents for the treatment of seed (fruits, tubers and grain) and of plant cuttings to protect them against fungus infections, as well as against phytopathogenic fungi occurring in the soil.

An important group of active substances comprises those compounds of the formula I wherein $R_3$ and $R_4$ form an additional bond. They are therefore compounds of the formula I which contain a cyclobutene ring.

A further group of important active substances is formed by those compounds of the formula I wherein one of $R_1$ and $R_6$ is hydrogen, methyl or ethyl, and the other is methyl or ethyl, $R_2$ and $R_3$ independently of one another are each hydrogen, fluorine or methyl, and $R_4$ and $R_5$ independently of one another are each hydrogen or methyl.

Preferred compounds of the formula I as active substances are those wherein $R_1 = R_6$ and $R_4 = R_5$, wherein therefore $R_1$ and $R_6$ have the same meaning and are methyl or ethyl, $R_2$ and $R_3$ independently of one another are each hydrogen, fluorine or methyl, and $R_4$ and $R_5$ have the same meaning and are hydrogen or methyl.

Particularly preferred are compounds of the formula I wherein $R_1$ and $R_6$ are each methyl, $R_2$ and $R_3$ independently of one another are hydrogen or fluorine, and $R_4$ and $R_5$ are each hydrogen. The particularly preferred individual compounds include the compounds Nos. 1, 2, 7, 9 and 15 mentioned in the following.

The compounds of the formula I can be produced in good yields, using a simple and economical process, by
(a) reaction of a compound of the formula II

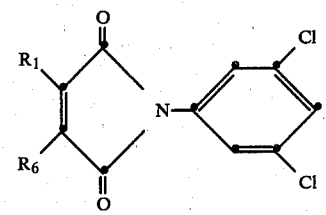

with a compound of the formula III

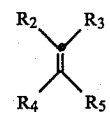

by irradiation at a wavelength shorter than 5000 Angström units, in the manner of a photochemical [2+2] cycloaddition, or
(b) stepwise reaction of a compound of the formula III with a compound of the formula IV

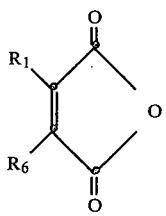

firstly by irradiation at a wavelength shorter than 5000 Ångström units, thus effecting photochemical [2+2] cycloaddition, to form a compound of the formula V

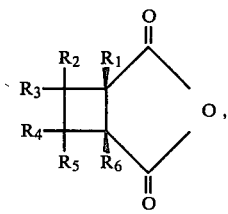

further reaction of this with 3,5-dichloroaniline to form an amidocarboxylic acid of the formula VI

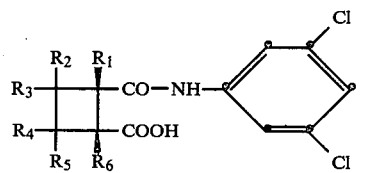

and subsequently cyclisation of VI by intramolecular removal of water, whereby $R_1$ to $R_6$ in the formulae II to VI have the meanings given for the formula I. The preferred method of production is that according to process variant (a).

The photochemical [2+2] cycloaddition reaction according to the invention of compounds of the formula III with compounds of the formula II or IV is favourable in particular also from the ecological viewpoint. The reaction proceeds surprisingly without dimers of maleic anhydrides or imides being formed, such as those always formed otherwise in comparable photochemical cycloaddition reactions [see for example Chem. Ber., 110, 2986–2995 (1977); Chem. Ber., 96, 498–508 (1962) and Chem. Ber., 98, 764–780 (1965); particularly Zhurnal Organicheskoi Khimii, Vol. 8, No. 2, pp. 377–382 (Feb. 1972)].

The photochemical [2+2] cycloaddition reaction of the compounds of the formula III with compounds of the formula II or IV is advantageously performed in the presence of an inert organic solvent at temperatures of between about −80° C. and +30° C., preferably between about −78° C. and −20° C.

Suitable inert organic solvents are for example: optionally chlorinated aliphatic or aromatic hydrocarbons, such as dichloromethane, 1,2-dichloroethane, 1,2,3-trichloropropane, 1,1,2,2-tetrachloroethane, benzene, chlorobenzene and dichlorobenzenes; aliphatic carboxylic acid esters, such as methyl acetate and ethyl acetate, dialkyl ethers having 2–6 C atoms in each of the alkyl parts, such as diethyl ether, di-n-propyl ether and di-isopropyl ether; cyclic ethers, such as dioxane and tetrahydrofuran; alkyl nitriles, particularly those having 2–5 C atoms, such as acetonitrile, propionitrile and butyronitrile. Preferred solvents are chlorinated aliphatic hydrocarbons, especially dichloromethane. Also suitable is acetone or methyl ethyl ketone.

Compounds known per se can be used as sensitisers for the photochemical cycloaddition reactions mentioned above, preferably such compounds which have an $E_T$ (triplet energy) of $\geq 230$ kJ/mol [see Paul S. Engel and Bruce M. Monroe "Advance in Photochemistry", Vol. 8, pp. 297–306, New York 1971]. Examples of sensitisers of this kind are benzophenone, acetophenone, m-methoxy-acetophenone, thioxanthone and biacetyl. The sensitiser preferably used is benzophenone. The sensitiser is in general used in an amount of about 0.5–10 percent by weight, relative to the starting compound of the formula II or IV.

For the photochemical reactions according to the invention, there can be used light sources which emit light at wavelengths of below 5000 Å, for example optionally metal-atom-doped high-pressure mercury vapour lamps, xenon vapour lamps, mercury-xenon lamps, mercury low-pressure or medium-pressure lamps, halogen lamps or $D_2$ lamps.

The photochemical reactions are advantageously carried out in a low-temperature irradiation apparatus. An approximately 2–20% solution of the compound of the formula II or IV together with the sensitiser is placed into the irradiation apparatus; the solution is then saturated, by way of a gas-inlet, with the desired compound of the formula III, and the reaction mixture is subsequently irradiated for about 2–10 hours depending on concentration, quantum yield and photon flux. The reaction product is processed for example by concentrating the reaction solution by evaporation, and recrystallising the crude product from suitable organic solvents, preferably from mixtures of dichloromethane and n-hexane. The resulting products of the formulae I and V, respectively, are analytically pure.

The reaction of the anhydrides of the formula V with 3,5-dichloroaniline is performed in a manner known per se, advantageously without solvent at temperatures of between about 80° and 120° C., or in an organic medium at temperatures of between about 20° and 120° C. Suitable organic solvents are for example: optionally chlorinated aliphatic or aromatic hydrocarbons, such as benzene, toluene, xylene, dichloromethane, chloroform, carbon tetrachloride and o-dichlorobenzene; aliphatic or cycloaliphatic ketones, such as acetone, methyl ethyl ketone, cyclopentanone and cyclohexanone; also dialkyl ethers having 2–6 C atoms in each of the alkyl parts, and cyclic ethers, such as tetrahydrofuran and dioxane.

Cyclisation of the amidocarboxylic acids of the formula VI with separation of water is performed thermally by customary methods, that is to say, by mere heating of the reaction mixture, or with the use of known dehydrating agents at temperatures between about 20° and 120° C. Suitable dehydrating agents are in particular anhydrides of aliphaic monocarboxylic acids which have 2–5 C atoms and which are unsubstituted or are substituted by halogen atoms or alkyl groups, such as anhydrides of acetic acid, propionic acid, butyric acid and valeric acid, and anhydrides of trichloro-, trifluoro-, trimethyl-, triethyl- and tri-n-butylacetic acid. A preferred dehydrating agent is acetic acid anhydride.

The reaction of the anhydrides of the formula I with 3,5-dichloroaniline can be performed also without the addition of solvents, the formed amidocarboxylic acids being then advantageously thermally cyclised, that is to say, by dry heating.

The starting compounds of the formulae II, III and IV and 3,5-dichloroaniline are known, and can be produced by methods known per say. Compounds of the formula II can be obtained for example by reaction of anhydrides of the formula IV with 3,5-dichloroaniline.

The invention also relates to the novel intermediates of the formula VI as well as to the intermediates of the formula V, particularly to compounds of the formula V wherein $R_1$ and $R_6$ have the same meaning and are methyl or ethyl, and $R_2$ to $R_5$ have the meanings defined under the formula I.

PRODUCTION EXAMPLES

Example 1

In a low-temperature irradiation apparatus, provided with a 125 W high-pressure mercury vapour lamp in a cooled Pyrex immersion well, stirrer and gas-inlet tube, 10 g (0.037 mol) of 2,3-dimethylmaleic acid-(3,5-dichlorophenyl)-imide and 1.0 g (0.0055 mol) of benzophenone in 220 ml of dichloromethane are introduced, and are cooled, by means of an external cooling bath containing an acetone/dry-ice mixture, to $-50°$ to $-55°$ C. Vinyl fluoride is now passed through this solution for 2 hours, and the solution is subsequently irradiated for 6 hours, during which time a weak flow of vinyl fluoride through the solution is maintained. The solvent is then evaporated off to leave 4.8 g of white crystals. Recrystallisation from dichloromethane/n-hexane yields 4.0 g (47% of theory) of 1,2-dimethyl-3-fluorocyclobutane-1,2-dicarboxylic acid-(3,5-dichlorophenyl)-imide in the form of white crystals; m.p. 122°–123° C. NMR spectrum (100 MHz, CDCl$_3$, δ in ppm): 1.4 (m, 6H, 2CH$_3$); 2.0–3.0 (m, 2H, —CH$_2$—); 4.6–5.4 (2m, —CHF—); 7.2–7.4 (m, 3H, aromat.). IR Spectrum (KBr, cm$^{-1}$, vs=very strong, s=strong, m=medium, w=weak): 1700$^{vs}$, 1590$^m$, 1585$^s$, 1450$^s$, 1450$^s$, 1360$^s$, 1150$^s$, 805$^s$. Compound No. 2.

Examples 2–6

In a manner analogous to that described in Example 1, there are produced:

1,2-dimethyl-cyclobutane-1,2-dicarboxylic acid-(3,5-dichlorophenyl)-imide, m.p. 149°–152° C., starting with 2,3-dimethylmaleic acid-(3,5-dichlorophenyl)-imide and ethylene Compound No. 1;

1,2,3-trimethyl-cyclobutane-1,2-dicarboxylic acid-(3,5-dichlorophenyl)-imide, m.p. 88°–89° C., starting with 2,3-dimethylmaleic acid-(3,5-dichlorophenyl)-imide and 1-propene: Compound No. 3;

3,3-difluoro-1,2-dimethyl-cyclobutane-1,2-dicarboxylic acid-(3,5-dichlorophenyl)-imide, m.p. 135°–140° C., starting with 2,3-dimethylmaleic acid-(3,5-dichlorophenyl)-imide and 1,1-difluoroethylene: Compound No. 4;

2-ethyl-1-methyl-cyclobutane-1,2-dicarboxylic acid-3,5-dichlorophenyl)-imide, m.p. 91°–93° C., starting with 2-ethyl-3-methylmaleic acid-(3,5-dichlorophenyl)-imide and ethylene: Compound No. 5; and 1,2,3,4-tetramethyl-cyclobutane-1,2-dicarboxylic acid-(3,5-dichlorophenyl)-imide, m.p. 81°–83° C., starting with 2,3-dimethylmaleic acid-(3,5-dichlorophenyl)-imide and trans-2-butene: Compound No. 6.

Example 7

(a) In a low-temperature irradiation apparatus, provided with a 125 W high-pressure mercury vapour lamp in a cooled Pyrex immersion well, stirrer and gas-inlet tube, 15 g (0.12 mol) of dimethylmaleic acid anhydride and 1 g of benzophenone (0.0054 mol) are dissolved in 300 ml of dichloromethane, and the solution is cooled, by means of an external cooling bath containing an isopropanol/dry-ice mixture, to $-60°$ to $-70°$ C.; ethylene is passed through for 1 hour, and the solution is irradiated at this temperature for 12 hours whilst a weak flow of ethylene passes through the solution. The solvent is then evaporated off, and the crude product is recrystallised from dichloromethane/n-hexane. The yield is 10 g of 1,2-dimethyl-cyclobutane-1,2-dicarboxylic acid anhydride (54% of theory) in the form of white crystals; m.p. 84°–86° C. NMR Spectrum (100 MHz), δ in ppm: 1.4 (s, 6H, 2CH$_3$); 2.0–2.5 (m, 4H, —CH$_2$C-H$_2$—). IR Spectrum (KBr, cm$^{-1}$, vs=very strong, s=strong, m=medium, w=weak): 2940$^m$, 1850$^s$, 1780$^{vs}$, 1470$^m$, 1445$^m$, 1300$^s$, 1280$^s$, 1240$^s$, 1170$^{vs}$, 970$^{vs}$, 950$^{vs}$ and 920$^{vs}$.

(b) 15.4 g (0.1 mol) of 1,2-dimethyl-cyclobutane-1,2-dicarboxylic acid anhydride are dissolved in 100 ml of toluene, and 16.2 g (0.1 mol) of 3,5-dichloroaniline are added. After 16 hours' stirring at 25° C., the colourless amidocarboxylic acid which has precipitated is separated. The yield is 27.8 g of 1-(3,5-dichlorophenylcarbamoyl)-1,2-dimethylcyclobutane-1-carboxylic acid (88% of theory), m.p. 164° C. NMR Spectrum (50 MHz) δ in ppm: 1.34 (s, 3H, CH$_3$); 1.45 (s, 3H, CH$_3$); 1.6–3.0 (m, 4H, —CH$_2$CH$_2$—); 6.9 (m, 1H, aromat.); 7.6 (m, 2H, aromat.); 8.75 (s, 1H, —COOH, exchangeable with D$_2$O).

Elementary analysis for C$_{14}$H$_{15}$Cl$_2$NO$_3$ (molecular weight 316.2): calculated: C 53.2% H 4.8% N 4.4% O 15.2% Cl 22.4%, found: C 53.3% H 4.7% N 4.7% O 15.2% Cl 22.5%.

(c$_1$) 14.3 g of the above amidocarboxylic acid in 100 ml of acetic anhydride are refluxed for 6 hours. After cooling, the imide which has precipitated is filtered off. The yield is 10.3 g (77% of theory) of 1,2-dimethyl-cyclobutane-1,2-dicarboxylic acid-(3,5-dichlorophenyl)-imide, the properties of which correspond to those of the compound produced according to Example 1.

(c$_2$) Cyclisation of the amidocarboxylic acid can also be performed by heating 3.2 g (0.01 mol) of 1-(3,5-dichlorophenylcarbamoyl)-1,2-dimethylcyclobutane-1-carboxylic acid for 2 hours at 160° C. After cooling, the crude product is recrystallised from ethyl acetate. The yield is 1.3 g (44% of theory) of 1,2-dimethyl-cyclobutane-1,2-dicarboxylic acid-(3,5-dichlorophenyl)-imide.

1,2-Dimethyl-cyclobutane-1,2-dicarboxylic acid-(3,5-dichlorophenyl)-imide can also be produced as follows:

(c$_3$) 7.7 g (0.05 mol) of 1,2-dimethylcyclobutane-1,2-dicarboxylic acid anhydride with 8.1 (0.05 mol) of 3,5-dichloroaniline are heated for 8 hours at 180° C. After cooling, the crude product is recrystallised from ethyl acetate to obtain 5.1 g (34% of theory) of 1,2-dimethyl-cyclobutane-1,2-dicarboxylic acid-(3,5-dichlorophenyl)-imide, the properties of which are identical to those of the compound produced according to Example 1.

(c$_4$) 7.7 g (0.05 mol) of 1,2-dimethylcyclobutan-1,2-dicarboxylic acid anhydride and 8.1 g (0.05 mol) of 3,5-dichloroaniline are dissolved in 100 ml of xylene, and the solution is refluxed for 8 hours with use of a water separator. The reaction solution is cooled, and the imide which has precipitated is filtered off. The yield is 11.6 g (78% of theory) of 1,2-dimethylcyclobutane-1,2-dicarboxylic acid-(3,5-dichlorophenyl)-imide.

Example 8

(a) By a procedure analogous to that described in Example 7 (a), 1-methyl-cyclobutane-1,2-dicarboxylic acid anhydride (m.p. 59°–60° C.) is produced by reaction of citraconic anhydride with ethylene.

(b) 10 g (0.07 mol) of 1-methyl-cyclobutane-1,2-dicarboxylic acid anhydride are dissolved in 50 ml of toluene, and 11.6 g (0.07 mol) of 3,5-dichloroaniline are added. After 24 hours' stirring at room temperature, the amide acid (m.p. 106°–108° C.) which has precipitated is separated. This amidocarboxylic acid is suspended in 40 ml of acetic anhydride, and the suspension is stirred for 24 hours at room temperature, in the course of which everything goes into solution. The acetic anhydride is evaporated off in a water-jet vacuum, and the pulverulent residue is recrystallised from dichloromethane/n-hexane to yield 15 g (73% of theory) of 1-methyl-cyclobutane-1,2-dicarboxylic acid-(3,5-dichlorophenyl)-imide, m.p. 110°–111° C. NMR Spectrum (100 MHz) δ in ppm: 1.55 (s, 3H, CH₃), 2.0–3.2 (m, 5H, —CH₂CH₂—CH—), 7.2–7.5 (m, 3H, aromat.). Compound No. 7.

The following compounds of the formula I are produced in a manner analogous to that of Example 8: ($R_5$=H):

| Comp. | $R_1$ | $R_6$ | $R_2$ | $R_3$ | $R_4$ | m.p. °C. |
|---|---|---|---|---|---|---|
| 8 | CH₃ | H | *CH₃[H] | H | *H[CH₃] | 123–128° |
| 9 | CH₃ | H | *F[H] | H | *H[F] | 106–109° |
| 10 | CH₃ | CH₃ | Cl | H | H | 140–143° |
| 11 | CH₃ | CH₃ | Cl | H | Cl | 192–197° |
| 12 | CH₃ | CH₃ | CH₃ | CH₃ | H | 96–98° |
| 13 | CH₃ | H | F | F | H | 176–178° |
| 14 | CH₃ | CH₃ | CH₃COO | H | H | 122–124° |

*place isomerism at positions $R_2$ and $R_4$

Example 9

Production of

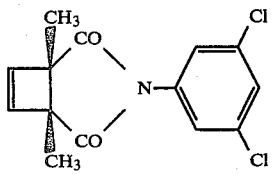

1,2-dimethyl-cyclobut-3-ene-1,2-dicarboxylic acid-(3,5-dichlorophenyl)-imide [Compound No. 15].

(a) In a manner according to that of Example 7 (a), acetylene is passed through 10 g (0.079 mol) of 2,3-dimethylmaleic acid anhydride and 1 g (0.0054 mol) of benzophenone in 250 ml of dichloromethane at −60° C. for 1 hour, and the reaction mixture is subsequently irradiated for 6 hours whilst a weak flow of acetylene is maintained. After the solvent has been evaporated off and the crude product has been recrystallised from dichloromethane/hexane, the yield is 7.5 g (62% of theory) of 1,2-dimethylcyclobut-3-ene-1,2-dicarboxylic acid anhydride, m.p. 84°–86° C.

(b) 6.9 g (0.0454 mol) of the intermediate produced according to (a) in 50 ml of toluene with 7.4 g (0.0454 mol) of 3,5-dichloroaniline are stirred for 24 hours at room temperature. The white precipitate obtained is stirred in 50 ml of acetic anhydride for 48 hours at room temperature and for 8 hours at 40° C. The oil obtained after concentration by evaporation is recrystallised from dichloromethane/hexane. The yield of final product is 3.6 g (27% of theory), m.p. 158°–160° C.

In a corresponding manner are obtained the following compounds of the formula I in which $R_3$ and $R_4$ form an additional bond in the four-membered ring:

| Compound | $R_1$ | $R_6$ | $R_2$ | $R_5$ | m.p. °C. |
|---|---|---|---|---|---|
| 16 | CH₃ | CH₃ | CH₃ | H | 142–143° |
| 17 | CH₃ | C₂H₅ | H | H | 137–140° |
| 18 | CH₃ | H | *CH₃[H] | *H[CH₃] | 129–135° |

*place isomerism

Any of the compounds of the formula I can in fact be produced by photochemical reaction both with the desired imide and with the desired anhydride (and subsequent further reaction with 3,5-dichloroaniline), that is to say, by either of the process variants (a) or (b) outlined in the test and further illustrated in the Examples 1 to 9.

The compounds of the formula I can be used on their own or together with suitable carriers and/or other additives. Suitble carriers and additives can be solid or liquid and they correspond to the substances common in formulation practice, such as natural or regenerated mineral substances, solvents, dispersing agents, wetting agents, adhesives, thickeners, binders and/or fertilisers. Active substances of the formula I can be used in admixture with other pesticidal preparations or with preparations for improving plant growth.

The content of active substance in commercial compositions is between 0.1 and 90%.

For application, the compounds of the formula I can be in the following forms (the weight-percentage figures in brackets signify advantageous amounts of active substance):

solid preparations: dusts and scattering agents (up to 10%), granulates [coated granules, impregnated granules and homogeneous granules] or pellets (1 to 80%);

liquid preparations:

(a) water-dispersible concentrates of active substance: wettable powders and pastes (25 to 90% in the commercial packing, 0.01 to 15% in ready-for-use solutions); emulsion concentrates and solution concentrates (10 to 50%; 0.01 to 15% in ready-for-use solutions);

(b) solutions (0.1 to 20%); or aerosols.

The active substances of the formula I of the present invention can be formulated for example as follows:

Wettable Powder

The following constituents are used to produce (a) a 70% wettable powder, (b) a 40% wettable powder, (c) a 25% wettable powder and (d) a 10% wettable powder:

(a)
70 parts of active substance,
5 parts of sodium dibutylnaphthalene sulfonate,
3 parts of naphthalenesulfonic acid/phenolsulfonic acid/formaldehyde condensate 3:2:1,
10 parts of kaolin, and 12 parts of Champagne chalk;

(b)
40 parts of active substance,
5 parts of sodium lignin sulfonate,
1 part of sodium dibutylnaphthalene sulfonate,
54 parts of silicic acid;

(c)
25 parts of active substance,
4.5 parts of calcium lignin sulfonate,
1.9 parts of Champagne chalk/hydroxyethyl cellulose mixture (1:1),
1.5 parts of sodium dibutylnaphthalene sulfonate,
19.5 parts of silicic acid,
19.5 parts of Champagne chalk, and
28.1 parts of kaolin; and (d)
10 parts of active substance,
3 parts of a mixture of the sodium salts of saturated fatty alcohol sulfates,
5 parts of naphthalenesulfonic acid/formaldehyde condensate, and
82 parts of kaolin.

The active substances are intimately mixed in suitable mixers with the additives, and the mixture is then ground in the appropriate mills and rollers. There are obtained wettable powders which have excellent wetting and suspension properties, and which can be diluted with water to give the suspensions of the desired concentration, and these suspensions are particularly suitable for leaf application.

Emulsifiable Concentrate

The following substances are used to produce a 25% emulsifiable concentrate:
25 parts of active substance,
2.5 parts of epoxidised vegetable oil,
10 parts of an alkylarylsulfonate/fatty alcohol polyglycol ether mixture,
5 parts of dimethylformamide, and
57.5 parts of xylene.

Emulsions of the concentration required can be prepared from these concentrates by dilution with water, and they are particularly suitable for leaf application.

Biological Examples

Residual protective action (a) Action against *Botrytis cinerea* on bean plants

Beans plants about 10 cm in height were sprayed with a spray liquor produced from wettable powder of the active substance (0.006% and 0.002%, respectively, of active substance), and after 48 hours, the treated plants were infested with a conidiospore suspension of the fungus. After incubation of the infested plants for 2-3 days with 95-100% relative humidity at 21° C., an assessment of the fungus infection was made. With an application concentration of 0.006%, all compounds of the formula I, namely compounds Nos. 1 to 18, effected complete prevention of infection (0-5% fungus infection). At a concentration of 0.002%, infection was completely prevented by compounds Nos. 1, 2, 5, 7, 9, 10, 15 and 16 (0-5% fungus infection), and was greatly reduced by the remainder of the 18 compounds listed (5-20% fungus infection).

(b) Action against *Sclerotinia fructigena* on apples

Artificially damaged apples were infested with *Sclerotinia fructigena* by transferring by pipette to each site of damage one drop of a mycelium suspension. After drying of the inoculum drop, the applies were sprayed with a wettable-powder suspension of the active substance (0.02% of active substance). The treated apples were placed into plastics containers and stored at 20°-22° C. for 14 days. An evaluation was made on the basis of the number of damage sites which had begun to rot. With compounds Nos. 1, 5, 7, 9, 10, 15 and 18, infection had been prevented almost completely (below 10% infection). No infection at all occurred after treatment with Compound No. 2.

(c) Action against *Erysiphe graminis* on barley plants

Residual protective action

Barley plants about 8 cm high were sprayed with a spray liquor produced from wettable powder of the active substance (0.02% of active substance). After 3-4 hours, the treated plants were dusted with conidia of the fungus. The infested barley plants were left in a greenhouse at about 22° C. and the level of fungus infection was assessed after 10 days. Fungus infection was completely prevented by, among others, Compounds Nos. 11, 12, 14 and 16.

(d) Action against Monilinia on cherry blossom or peach blossom (Monilinia infection on stone fruit)

A number of completely blossomed stone-fruit branches were sprayed with a spray liquor produced from an emulsion concentrate (containing 0.025% of active substance). A few hours later, the blossom clusters were cut off, placed with the stems into the moist sand contained in plastic dishes and inoculated with a spore suspension. The dishes were then loosely covered with transparent plastic sheet and were kept at room temperature for 2 days. The extent of infection was estimated on the basis of the number of infected blossoms, 40 blossoms being used per active substance. The compounds Nos. 1 to 18 effected a reduction of infection to below 20%. Some compounds prevented infection completely, for example Compounds Nos. 2 and 7.

What is claimed is:

1. A method for combatting plant pathogenic fungi which comprises applying to plants infested with such fungi, or to the locus of said plant, a fungicidally or fungistatically effective amount of 1,2-dimethyl-3-fluoro-cyclobutan-1,2-dicarbonic acid-(3,5-dichlorophenyl)-imide.

2. A method for combatting plant pathogenic fungi which comprises applying to plants infested with such fungi, or to the locus of said plants, a fungicidally or fungistatically effective amount of 1,2-dimethyl-3,3-difluoro-cyclobutane-1,2-dicarbonic acid-(3,5-dichlorophenyl)-imide.

3. A method for combating plant pathogenic fungi which comprises applying to plants infested with such fungi, or to the locus of said plants, a fungicidally or fungistatically effective amount of 1-methyl-3,3-difluoro-cyclobutane-1,2-dicarbonic acid-(3,5-dichlorophenyl)-imide.

* * * * *